United States Patent [19]
Goto et al.

[11] Patent Number: 5,783,428
[45] Date of Patent: Jul. 21, 1998

[54] METHOD OF PRODUCING FUMARIC ACID

[75] Inventors: Makoto Goto; Terukazu Nara; Izuru Tokumaru; Nobutake Fugono; Yasukazu Uchida; Masato Terasawa; Hideaki Yukawa, all of Inashiki-gun, Japan

[73] Assignee: Mitsubishi Chemical Corporation, Tokyo, Japan

[21] Appl. No.: 804,144

[22] Filed: Feb. 20, 1997

Related U.S. Application Data

[63] Continuation of Ser. No. 503,645, Jul. 18, 1995, abandoned.

[30] Foreign Application Priority Data

| | | | |
|---|---|---|---|
| Jul. 19, 1994 | [JP] | Japan | 6-167103 |
| Mar. 30, 1995 | [JP] | Japan | 7-097956 |
| May 15, 1995 | [JP] | Japan | 7-139994 |

[51] Int. Cl.$^6$ .................. C12P 7/46; C12P 13/20
[52] U.S. Cl. .................. 435/145; 435/109; 435/832; 435/833
[58] Field of Search .................. 435/145, 832, 435/833

[56] References Cited

U.S. PATENT DOCUMENTS

| | | | |
|---|---|---|---|
| 2,816,923 | 12/1957 | Stephenson | 260/537 |
| 2,955,136 | 10/1960 | Sullivan et al. | 260/537 |
| 3,214,345 | 10/1965 | Chibata et al. | 195/30 |
| 3,310,475 | 3/1967 | Yamatodani et al. | 195/30 |
| 3,332,992 | 7/1967 | Brown et al. | 260/537 |
| 3,391,059 | 7/1968 | Takamura et al. | 195/30 |

FOREIGN PATENT DOCUMENTS

| | | |
|---|---|---|
| 0 127 940 | 12/1984 | European Pat. Off. . |
| 42-11993 | 7/1967 | Japan . |
| 42-11994 | 7/1967 | Japan . |
| 42-11996 | 7/1967 | Japan . |
| 61-29718 | 7/1986 | Japan . |

OTHER PUBLICATIONS

Otsuka Agr Bio Chem vol. 25 No. 9, pp. 726–730 (1961). "As–Trans Isomerase".

Kitahara et al., Amino Acids Fermentation and Metabolism, vol. 1, p. 102, (1959).

Takahashi et al., Amino Acids Fermentation and Metabolism, vol. 7, p. 23 (1963).

Watanabe et al., Nippon Nogeikagaku Kaishi, vol. 38, p. 434 (1964).

Otsluka, Agr. Biol. Chem., vol. 25, No. 9, pp. 726–730 (1961).

Takamura et al., Agr. Biol. Chem., vol. 33, No. 5 pp. 718–728 (1969).

Scher et al., The Journal of Biological Chemistry, vol. 244, No. 7, No. 7, Apr. 10, 1969, pp. 1878–1882.

*Primary Examiner*—Herbert J. Lilling
*Attorney, Agent, or Firm*—Wenderoth, Lind & Ponack

[57] ABSTRACT

Fumaric acid is produced by reacting a culture of a microorganism which produces maleate isomerase that exhibits a maximum activity at not less than 50° C. or a treated product thereof with maleic acid in an aqueous solution, and isomerizing maleic acid to produce fumaric acid. L-aspartic acid is produced by reacting both of a culture of a microorganism which produces maleate isomerase or a treated product thereof and a culture of a microorganism which produces aspartase or a treated product thereof with maleic acid and ammonia in an aqueous solution, producing L-aspartic acid from maleic acid and ammonia by enzyme reactions, and recovering L-aspartic acid from the reaction mixture.

11 Claims, No Drawings

METHOD OF PRODUCING FUMARIC ACID

This application is a continuation of now abandoned application Ser. No. 08/503,645, filed Jul. 18, 1995.

TECHNICAL FIELD

The present invention relates to a method of producing fumaric acid, and in particular relates to a method of producing fumaric acid useful as a material for various fine chemicals such as aspartic acid, malic acid, and alanine by isomerizing maleic acid by utilizing a thermophilic microorganism which produces heat-stable maleate isomerase. The present invention also relates to a method of efficiently producing L-aspartic acid from maleic acid.

BACKGROUND OF THE INVENTION

Chemical methods have been predominantly proposed as methods of producing fumaric acid by isomerizing maleic acid (U.S. Pat. Nos. 2,816,923, 2,955,136, and 3,332,992). However, these methods have problems in that the ratio of conversion to fumaric acid is restricted by reaction equilibrium, maleic acid or fumaric acid is deteriorated because these methods reside in a reaction at a high temperature, and the yield decreases due to formation of by-products.

On the other hand, in relation to production of fumaric acid by using an enzyme reaction, it is known that maleate isomerase (maleate cis-trans-isomerase) isomerizes maleic acid to fumaric acid. Microorganisms which are known to produce maleate isomerase are as follows: Pseudomonas sp. [K. Otsuka, *Agric. Biol. Chem.*, Vol. 25, No. 9, p. 726 (1961)], *Alcaligenes faecalis* IB-14 [Takamura, *Agric. Biol. Chem.*, Vol. 33, p. 718 (1969)], and *Pseudomonas fluolescens* ATCC 23728 [Scher, *J. Biol. Chem.*, Vol. 244, p. 1878 (1969)]. However, only the enzymatic properties of maleate isomerases produced by these organisms have been reported. Details such as molecular weight, subunit structure, amino acid sequence, and nucleotide sequence of DNA of the enzymes have been not yet clarified. Further, no investigation about industrial application of maleate isomerase has been made at all as far as the present inventors know.

It has been reported that maleate isomerase having been known until now is unstable even at a moderate temperature, and its activity greatly decreases at a high temperature [Takamura, *Agric Biol. Chem.*, Vol. 33, p. 718 (1969)]. In the production process for fumaric acid by using maleate isomerase, in general, when the reaction temperature is raised, the rate of reaction and the productivity of fumaric acid are increased. However, the enzyme which serves as a catalyst is inactivated by heat when the reaction temperature is raised. And the enzymatic life of the catalyst becomes short. Therefore, the process which has high productivity of fumaric acid may be constructed by using a heat-stable maleate isomerase.

On the other hand, L-aspartic acid is produced mainly from fumaric acid and ammonia by an enzymatic method, and widely utilized for food additives and transfusion fluids. The known methods for producing aspartic acid from fumaric acid by the enzymatic method are as follows: a method using *Escherichia coli* [Kitahara et al., *Amino Acids Fermentation and Metabolism*, Vol. 1, p. 102 (1959)], a method using a bacterium belonging to the genus Pseudomonas [Takahashi et al., *Amino Acids Fermentation and Metabolism*, Vol. 7, p. 23 (1963), U.S. Pat. No. 3,310,475], and a method using a bacterium belonging to the genus Brevibacterium [Watanabe et al., *Nippon Nogeikagaku Kaishi*, Vol. 38, p. 434 (1964), Japanese Patent Publication No. 61-29718].

Maleic acid is obtained more inexpensively than fumaric acid. Maleic acid is more advantageous as a raw material for aspartic acid. A method of producing aspartic acid from maleic acid is known, including a method of obtaining aspartic acid by using microbial cells which produce aspartic acid from maleic acid [Japanese Patent Publication Nos. 42-11993, 42-11994 and 42-11996, and U.S. Pat. No. 3,391,059]. However, the yield of aspartic acid versus material, and the rate of aspartic acid formation have been not considered to be sufficient. The molar yield of L-aspartic acid with respect to a theoretical yield described in U.S. Pat. No. 3,391,059 is 92%.

A method of producing L-aspartic acid from maleic acid is known, in which maleic acid is isomerized by using a Br catalyst, and an aspartate-producing microorganism is allowed to react on formed fumaric acid [U.S. Pat. Nos. 2,955,136 and 3,332,992]. However, there have been problems in that the yield of isomerization is not sufficient because of using a chemical catalyst, and impurities are apt to form due to reacting at a high temperature during the isomerization.

SUMMARY OF THE INVENTION

An object of the present invention is to provide a method of producing fumaric acid by utilizing maleate isomerase which stably maintains its activity under a moderate temperature condition as a matter of course as well as under a high temperature condition.

Another object of the present invention is to provide a method of producing L-aspartic acid with a high yield and a good efficiency from maleic acid and ammonia in accordance with a new viewpoint.

In order to isolate a microorganism which can grow under a high temperature condition, and can produce maleate isomerase, the present inventors have tried to isolate a microorganism which can grow under a high temperature condition on a medium containing maleic acid as a sole carbon and energy source, and which has maleate isomerase. Further, in order to establish an efficient method of producing L-aspartic acid, the present inventors have made diligent investigations. As a result, the present inventors have found that L-aspartic acid is produced efficiently at a high yield by reacting both a culture of a microorganism which produces maleate isomerase or a treated product thereof and a culture of a microorganism which produces aspartase or a treated product thereof with maleic acid, and ammonia in an aqueous solution. Two types of enzyme reactions are conducted simultaneously in a reactor. And, the present invertors have found that the yield and the efficiency can be further improved by maintaining the concentration of fumaric acid produced by isomerization of maleic acid in the reaction solution so that it is not more than 0.5% (wt/vol). Thus the present invention has been completed.

Thus, according to the present invention, there is provided a method of producing fumaric acid comprising the steps of reacting a culture of a microorganism which produces maleate isomerase that exhibits a maximum activity at not less than 50° C. or a treated preparation thereof with maleic acid in an aqueous solution, and isomerizing maleic acid by an enzyme reaction in the mixed solution to produce fumaric acid. The microorganism described above is exemplified by microorganisms belonging to the genus Bacillus capable of growing at a temperature above 40° C. The "microorganism which produces maleate isomerase" referred to herein means microorganisms per se isolated from the nature, and derivative strains obtained from them by a mutation treatment, as well as transformant strains obtained by introducing a maleate isomerase gene originating from these microorganisms. The "maximum activity" means the maximum value of specific activity when the activity of maleate isomerase is measured under various temperature conditions in accordance with a method of W. Scher [W. Scher and W. B. Jakoby, *J. Biological Chem.*, Vol. 211, p. 1878 (1969)] or the like.

According to the present invention, there is also provided a method of producing L-aspartic acid comprising the steps of mixing a culture of a microorganism which produces maleate isomerase or a treated product thereof, a cultured microorganism which produces aspartase or a treated product thereof, maleic acid, and ammonia in an aqueous solution, producing L-aspartic acid from maleic acid and ammonia by enzyme reactions in the mixed solution, and collecting L-aspartic acid from the reaction solution. In this method, the microorganism which produces maleate isomerase is exemplified by microorganisms belonging to the genus Bacillus capable of growing at a temperature above 40° C. Further, as a preferred embodiment of the method of producing L-aspartic acid of the present invention, there is provided a method according to the aforementioned method, in which the concentration of fumaric acid produced by isomerization of maleic acid in the reaction solution is maintained at not more than 0.5% (wt/vol).

The present invention will be described in detail below.

1. Method of producing fumaric acid

The "maleate isomerase (maleate cis-trans-isomerase; EC 5.2.1.1.)" in the present invention means an enzyme which catalyzes a reaction to isomerize maleic acid (cis form) to produce fumaric acid (trans form).

Any method is available without any special limitation for obtaining the microorganism which produces maleate isomerase of the present invention provided that microbial cells or a culture liquid obtained by cultivation in a medium has the enzyme activity irrelevant to whether the enzyme is constitutively expressed or inducibly produced by an inducing substance, temperature or the like. An example may be described as follows as a method to enable isolation and preparation from nature.

(1) Isolation of maleate-assimilating microorganisms

A sample obtained from nature is placed in a medium containing maleic acid as a sole carbon and energy source, for example, medium A [composition: disodium maleate 5 g, $KH_2PO_4$ 0.7 g, $K_2HPO_4$ 1.4 g, $NH_4NO_3$ 1 g, $MgSO_4.7H_2O$ 0.2 g, biotin 0.2 mg, thiamin hydrochloride 0.2 mg, $FeSO_4.7H_2O$ 20 mg, $MnSO_4$ 20 mg, distilled water 1 L (pH 7.2)] to perform cultivation with shaking at 40°–70° C. for 2–4 days. A culture after the cultivation is spread on a plate medium having the composition of the medium A containing 2% agar, and cultivated at 40°–70° C. for 2–4 days. Colonies grown on the plate medium are isolated, and subjected to a detection test for the maleate isomerase activity described below to select microorganisms which produce maleate isomerase.

(2) Selection of microorganisms which produce maleate isomerase

The microorganisms isolated in the item (1) described above are cultivated with shaking at 40°–70° C. for 1–2 days using the medium A, and microbial cells are collected by centrifugation. Obtained microbial cells are suspended in reaction solution A [composition: maleic acid 30 g, 25% aqueous ammonia 40 ml, Triton X-100 0.5 g, distilled water 1 L], and shaken overnight at 40°–70° C., and then supernatant solutions are recovered by centrifugation. Microorganisms which produce maleate isomerase can be selected by confirming production of fumaric acid in the obtained supernatants of the reaction solutions.

Any method for confirming fumaric acid is available without any special limitation. However, the fumaric acid can be confirmed by HPLC analysis using a column for organic acid analysis to make detection by using an ultraviolet detector, paper chromatography, or enzymatic methods utilizing enzymes such as fumarase, malate dehydrogenase, and aspartase.

The microorganism which can be obtained as described above may be exemplified by microorganisms belonging to the genus Bacillus isolated by the present inventors, for example, *Bacillus stearothermophilus* MI-101 strain, *Bacillus stearothermophilus* MI-102 strain, *Bacillus brevis* MI-103 strain, *Bacillus brevis* MI-104 strain, and *Bacillus* sp. MI-105 strain. These microorganisms have bacteriological properties described in detail below, each of which is considered to be a novel microorganism.

A) MI-101 strain (i) Morphological properties

Form: rod

Spore: formed (elliptical, position: terminal or subterminal, sporangium: not distended)

Gram stain: positive

Mobility: absent (ii) Physiological properties

Attitude to oxygen: aerobic

Growth under anaerobic condition: no growth

Catalase: positive

V-P reaction: negative

H of V-P broth: 5.6

Production of acid from glucose: positive

Production of gas from glucose: negative

Liquefaction of gelatin: positive

Decomposition of starch: positive

Utilization of citrate: negative

Utilization of propionate: negative

Egg yolk reaction: negative

Reduction of nitrate: positive

Growth at pH 6.8 (nutrient broth): positive

Growth at pH 5.7: negative

Growth in the presence of 5% NaCl: negative

Growth in the presence of 7% NaCl: negative

Growth at 10° C.: negative

Growth at 30° C.: negative

Growth at 40° C.: positive

Growth at 55° C.: positive

Growth at 65° C.: positive

Growth at 70° C.: positive

Maleate isomerase activity: present

GC content of intracellular DNA (mole %): 42%

It has been revealed that the bacteriological properties described above reside in a novel bacterial strain belonging to the genus *Bacillus stearothermophilus* as a result of investigation in accordance with *Bergey's Manual of Systematic Bacteriology*, Vol. 2, [P. H. A. Sneath, N. S. Mair, M. E. Sharpe and J. G. Hol (1986) Williams & Wilkins]. The present inventors designated this bacterium as *Bacillus stearothermophilus* MI-101 strain. This bacterium has been deposited on Mar. 7, 1995 in National Institute of Bioscience and Human Technology 10-3, Higashi 1-chrome, Tsukuba-shi, Ibaraki-ken 305, Japan under a deposition number of FERM P-14801, transferred to international deposition based on the Budapest Treaty on Jul. 12, 1995, and deposited under a deposition number of FERM BP-5160.

B) MI-102 strain (i) Morphological properties

Form: rod

Spore: formed (elliptical, position: terminal or subterminal, sporangium: not distended)

Gram stain: positive

Mobility: present (ii) Physiological properties

Attitude to oxygen: aerobic

Growth under anaerobic condition: no growth

Catalase: positive

V-P reaction: weakly positive pH of V-P broth: 5.5

Production of acid from glucose: positive

Production of gas from glucose: negative

Liquefaction of gelatin: positive

Decomposition of starch: positive

Utilization of citrate: positive

Utilization of propionate: negative

Egg yolk reaction: negative

Reduction of nitrate: positive

Growth at pH 6.8 (nutrient broth): positive

Growth at pH 5.7: positive

Growth in the presence of 5% NaCl: negative

Growth in the presence of 7% NaCl: negative

Growth at 10° C.: negative

Growth at 30° C.: negative

Growth at 40° C.: positive

Growth at 55° C.: positive

Growth at 65° C.: positive

Growth at 70° C.: positive

Maleate isomerase activity: present

GC content of intracellular DNA (mole %): 54%

It has been revealed that the bacteriological properties described above reside in a novel bacterial strain belonging to the genus *Bacillus stearothermophilus* as a result of investigation in accordance with *Bergey's Manual of Systematic Bacteriology* [supra]. The present inventors designated this bacterium as *Bacillus stearothermophilus* MI-102 strain. This bacterium has been deposited on Mar. 7, 1995 in National Institute of Bioscience and Human Technology under a deposition number of FERM P-14802, transferred to international deposition based on the Budapest Treaty on Jul. 12, 1995, and deposited under a deposition number of FERM BP-5161.

C) MI-103 strain (i) Morphological properties

Form: rod

Spore: formed (elliptical, position: terminal or subterminal, sporangium: slightly distended)

Gram stain: positive

Mobility: present (ii) Physiological properties

Attitude to oxygen: aerobic

Growth under anaerobic condition: no growth

Catalase: positive

V-P reaction: negative pH of V-P broth: 7.2

Production of acid from glucose: positive

Production of gas from glucose: negative

Liquefaction of gelatin: negative

Decomposition of starch: negative

Utilization of citrate: positive

Utilization of propionate: positive

Egg yolk reaction: negative

Reduction of nitrate: positive

Growth at pH 6.8 (nutrient broth): positive

Growth at pH 5.7: negative

Growth in the presence of 5% NaCl: negative

Growth in the presence of 7% NaCl: negative

Growth at 10° C.: negative

Growth at 30° C.: positive

Growth at 40° C.: positive

Growth at 55° C.: positive

Growth at 65° C.: negative

Growth at 70° C.: negative

Maleate isomerase activity: present

GC content of intracellular DNA (mole %): 51%

It has been revealed that the bacteriological properties described above reside in a novel bacterial strain belonging to the genus *Bacillus brevis* as a result of investigation in accordance with *Bergey's Manual of Systematic Bacteriology* [supra]. The present inventors designated this bacterium as *Bacillus brevis* MI-103 strain. This bacterium has been deposited on Mar. 7, 1995 in National Institute of Bioscience and Human Technology under a deposition number of FERM P-14803, transferred to international deposition based on the Budapest Treaty on Jul. 12, 1995, and deposited under a deposition number of FERM BP-5162.

D) MI-104 strain (i) Morphological properties

Form: rod

Spore: formed (elliptical, position: terminal or subterminal, sporangium: slightly distended)

Gram stain: positive

Mobility: present (ii) Physiological properties

Attitude to oxygen: aerobic

Growth under anaerobic condition: no growth

Catalase: positive

V-P reaction: negative pH of V-P broth: 7.2

Production of acid from glucose: positive

Production of gas from glucose: negative

Liquefaction of gelatin: negative

Decomposition of starch: negative

Utilization of citrate: positive

Utilization of propionate: positive

Egg yolk reaction: negative

Reduction of nitrate: positive

Growth at pH 6.8 (nutrient broth): positive

Growth at pH 5.7: negative
Growth in the presence of 5% NaCl: negative
Growth in the presence of 7% NaCl: negative
Growth at 10° C.: negative
Growth at 30° C.: positive
Growth at 40° C.: positive
Growth at 55° C.: positive
Growth at 65° C.: negative
Maleate isomerase activity: present
GC content of intracellular DNA (mole %): 50%

It has been revealed that the bacteriological properties described above reside in a novel bacterial strain belonging to the genus *Bacillus brevis* as a result of investigation in accordance with *Bergey's Manual of Systematic Bacteriology* [supra]. The present inventors designated this bacterium as *Bacillus brevis* MI-104 strain. This bacterium has been deposited on Mar. 7, 1995 in National Institute of Bioscience and Human Technology under a deposition number of FERM P-14804, transferred to international deposition based on the Budapest Treaty on Jul. 12, 1995, and deposited under a deposition number of FERM BP-5163.

E) MI-105 strain (i) Morphological properties
    Form: rod
    Spore: formed (elliptical, position: terminal or subterminal, sporangium: slightly distended)
    Gram stain: positive
    Mobility: present (ii) Physiological properties
    Attitude to oxygen: aerobic
    Catalase: positive
    Growth at 30° C.: negative
    Growth at 40° C.: positive
    Growth at 55° C.: positive
    Maleate isomerase activity: present It has been revealed that the bacteriological properties described above reside in a novel bacterial strain belonging to the genus Bacillus as a result of investigation in accordance with *Bergey's Manual of Systematic Bacteriology* [supra]. The present inventors designated this bacterium as Bacillus sp. MI-105 strain. This bacterium has been deposited on Mar. 7, 1995 in National Institute of Bioscience and Human Technology under a deposition number of FERM P-14805, transferred to international deposition based on the Budapest Treaty on Jul. 12, 1995, and deposited under a deposition number of FERM BP-5164.

Next, there will be described an example of the method for producing maleate isomerase by using the microorganism as described above, and isomerizing maleic acid to produce fumaric acid.

(3) Production of maleate isomerase, and production of fumaric acid from maleic acid by using maleate isomerase Maleic acid can be isomerized to produce fumaric acid by mixing maleic acid with a culture of the microorganism which produces maleate isomerase isolated as described in the item (2) or a treated product thereof in an aqueous solution. The "culture" means microbial cells obtained from the medium after cultivating the microorganism. The "treated product" means an immobilized product obtained by immobilizing the culture recovered from the medium, a ruptured product obtained by sonicating the microbial cells by means of sonication, crush and so on, an extracted product obtained by extracting the ruptured product with water or the like, crude enzyme or purified enzyme of maleate isomerase obtained by subjecting the extracted product to treatments of ammonium sulfate salting out, column chromatography and so on, and an immobilized product obtained by immobilizing the ground product, the extracted product, the enzyme component and so on.

The concept of "mixing maleic acid with a culture of the microorganism or a treated product thereof in an aqueous solution" includes addition of a culture of the microorganism or a treated product thereof to an aqueous solution containing maleic acid, addition of maleic acid to an aqueous solution containing a culture of the microorganism or a treated product thereof, and passage through of an aqueous solution containing maleic acid to a column charged with immobilized microbial cells or a treated product thereof.

The microorganism which produces maleate isomerase can be cultivated by using an ordinary nutrient medium containing a carbon source, a nitrogen source, inorganic salts, various vitamins and so on. As the carbon source, there may be used, for example, maleic acid, saccharides such as glucose, sucrose, fructose and maltose, alcohols such as ethanol and methanol, organic acids such as citric acid and maleic acid, and waste molasses, preferably maleic acid or a mixture of maleic acid and other carbon sources. As the nitrogen source, for example, ammonia, ammonium sulfate, ammonium chloride, ammonium nitrate, urea, etc. are used singly or in combination. As the inorganic salts, for example, dipotassium hydrogenphosphate, potassium dihydrogenphosphate, magnesium sulfate, etc. are used. In addition, nutrients such as peptone, meat extract, yeast extract, corn steep liquor, casamino acid, various vitamins such as biotin, etc. can be added to the medium. Further, maleic acid, malonic acid, tartronic acid, citraconic acid, mesaconic acid, etc. may be added to the medium as an inducing substance for maleate isomerase.

The culture condition is not specifically limited provided that a temperature is given at which the maleate isomerase-producing microorganism can grow usually under an aerobic condition of aeration, agitation, shaking, etc. pH is also not specifically limited during cultivation provided that pH is given at which the microorganism can grow. pH can be adjusted during cultivation by adding acid or alkali.

The microbial cells containing maleate isomerase can be obtained by collecting microbial cells from a culture thus obtained by centrifugation and so on.

Any known method for purifying enzyme can be applied as a method for extracting and purifying maleate isomerase from the microbial cells. As a destruction method for microbial cells, for example, there may be used a mechanical destruction method using sonication, French Press, homogenizer and so on, or an enzymatic destruction method using lysozyme and so on. A soluble fraction of a destroyed product of microbial cells thus obtained or its fractionated product may be used as a crude enzyme fraction of maleate isomerase. Purified enzyme obtained by further purifying the crude enzyme fraction may be used. Purification of maleate isomerase from the crude enzyme fraction can be usually carried out by (a) separation by a precipitation method, for example, an ammonium sulfate precipitation method, (b) separation by chromatography, for example, ion exchange chromatography, affinity absorption chromatography, and gel filtration chromatography, (c) a separation method by an electrophoresis method, and (d) an optional combination of these methods. An example will be described in detail in Test Example 1.

In the purification process as described above, the fraction containing maleate isomerase can be detected by measuring the maleate isomerase activity using the decrease in substrate maleic acid as the decrease in absorbance at 240 nm in the presence of fumarase originating from swine heart in accordance with a method of Otsuka et al. [*Agric. Biol. Chem.*, Vol. 25, p. 726 (1961)]. The maleate isomerase activity can be also measured in accordance with a method of W. Scher. Namely, the specific activity of maleate isomerase can be determined by adding purified maleate isomerase to a reaction solution [composition: 200 mM potassium phosphate buffer (pH 7.2), 0.5 mM dithiothreitol, 10 mM disodium maleate], and measuring the rate of formation of fumaric acid at each temperature as the rate of increase of absorbance at 290 nm by using a spectrophotometer for 10 minutes.

The purity and the molecular weight of purified maleate isomerase can be known by conducting polyacrylamide gel electrophoresis in accordance with a method of Davis [B. J. Davis, *Ann. N. Y. Acad. Sci.*, Vol. 121, p. 404 (1964)] or a method of Laemmli [U. K. Laemmli, *Nature*, Vol. 227, p. 680 (1970)], and detecting the protein by staining the gel by using, for example, a Coomassie Blue dye solution [composition: 0.2% (v/v) Coomassie Brilliant Blue R 250, 40% (v/v) methanol, 10% (v/v) acetic acid], or a commercially available silver staining kit (for example, produced by Wako Pure Chemical) to detect the protein.

When microbial cells of the microorganism which produces maleate isomerase obtained as described above are immobilized to a carrier, microbial cells recovered from a culture as they are, or microbial cells washed with an appropriate buffer, for example, a phosphate buffer of about 0.02–0.2M (pH 6–10) can be used. The crude enzyme fraction or the purified enzyme of maleate isomerase extracted and purified from microbial cells as described above may be immobilized to a carrier to be also used for the method of producing fumaric acid of the present invention.

Microbial cells, or a ruptured, extracted or purified preparation of microbial cells may be immobilized in accordance with a per se known and usually used method by using a method of immobilization to an appropriate carrier such as acrylamide monomer, alginic acid, or K-carageenan. Specifically, for example, microbial cells can be immobilized as follows. Sodium alginate is dissolved in hot water at 60°–70° C. to prepare an aqueous solution of 50 g/L of sodium alginate, followed by cooling to room temperature. Washed microbial cells (15 g) and water are added to the aqueous solution (60 ml) to give a total volume of 100 ml, followed by sufficient mixing. The mixed solution is added dropwise to an aqueous solution of 0.1M calcium chloride (400 ml), and agitated as it is for 1 hour to obtain 50 g of spherical calcium alginate gel. Next, an aqueous solution of polyethyleneimine (50 g/L) is neutralized with conc. sulfuric acid, to which 2.75 g of N-(3-dimethylamino)propyl-N'-ethylcarbodiimide hydrochloride is added to obtain a crosslinking solution (245 ml) to which the total amount of the aforementioned gel is added, followed by gentle agitation at 23° C. for 12 hours. This reaction mixture is filtered and washed, and thus the objective immobilized microbial cells can be obtained.

A ruptured, extracted or purified product of microbial cells can be immobilized in the same manner. The amounts of sodium alginate, polyethyleneimine, and N-(3-dimethylamino)propyl-N'-ethylcarbodiimide hydrochloride to be used may be suitably set depending on the amount and type of microbial cells or a treated product thereof to be used.

The aqueous solution used for the isomerization reaction of maleic acid can be an aqueous solution or an appropriate buffer, for example, a phosphate buffer of about 0.02–0.2M (pH 6–10) containing maleic acid. In order to further enhance the substance permeability of cell membrane of microbial cells, toluene, xylene, nonionic surfactant or the like can be added to the aqueous solution in an amount of 0.05–2% (w/v).

The concentration of maleic acid to serve as a reaction material in the aqueous solution is appropriately about 0.1–2M. With respect to the form of maleic acid, forms of acid or salt as well as its anhydride can be used. Maleic anhydride is easily converted into maleic acid when it is provided in an aqueous solution. The salt of maleic acid may be exemplified by sodium salt, potassium salt, ammonium salt and so on.

The enzyme reaction temperature and pH in the aqueous solution described above are not specifically limited. However, it is suitable that the temperature is usually 10°–60° C., preferably 30°–50° C., and pH in the reaction solution may be 5–10, preferably about 6–9. pH can be adjusted by adding acid or alkali. Especially, according to the method of the present invention, the isomerization reaction of maleic acid can be stably conducted at a normal temperature as a matter of course, as well as at a high temperature above 40° C.

The aqueous solution containing fumaric acid thus obtained can be used as it is as a material for production of various useful substances such as fine chemicals. For example, malic acid, aspartic acid, alanine, etc. can be produced by adding various enzymes which use fumaric acid as a substrate or microbial cells containing them, for example, fumarase, aspartame, etc. or microbial cells containing these enzymes, in the same reaction vessel as that used for conducting the isomerization reaction of maleic acid, or in a separate reaction vessel.

For example, aspartic acid can be produced by allowing maleate isomerase to act in an aqueous solution containing maleic acid, and then allowing aspartase (EC 4.3.1.1) to act in the co-presence of ammonium ion. Further, alanine can be produced by allowing aspartate decarboxylase (EC 4.1.1.12) to act in the aqueous solution containing aspartic acid.

Malic acid can be produced by allowing fumarase (EC 4.2.1.2) to act in the aqueous solution containing fumaric acid produced by maleate isomerase. As aspartase, aspartate decarboxylase, and fumarase referred to herein, any one originating from any biological source may be used provided that it has any of these enzyme activities. Any of cells containing these enzymes, crude enzyme fractions of these enzymes, or purified enzymes can be allowed to act in accordance with any of methods known until now provided that the enzyme reaction can be conducted.

Fumaric acid produced by the aforementioned method can be obtained as crystals by separating it from the microbial cells and the treated preparation thereof by means of ultrafiltration membrane separation, centrifugation, etc., and then precipitating it by means of a known method such as sulfate isoelectric precipitation, followed by washing with water and drying.

Next, properties of the maleate isomerase produced by the microorganisms of the present invention will be explained with reference to Test Examples.

Test Example 1: Purification of maleate isomerase produced by Bacillus stearothermophilus MI-101 strain, and measurement of enzyme activity at not less than 50° C.

(1) Purification of maleate isomerase

Medium A [composition: disodium maleate 5 g, $KH_2PO_4$ 0.7 g, $K_2HPO_4$ 1.4 g, $NH_4NO_3$ 1 g, $MgSO_4 \cdot 7H_2O$ 0.2 g, biotin 0.2 mg, thiamin hydrochloride 0.2 mg, $FeSO_4 \cdot 7H_2O$ 20 mg, $MnSO_4$ 20 mg, distilled water 1 L (pH 7.2)] (3 L)

was introduced into a jar fermenter having a volume of 5 L, and sterilized at 121° C. for 20 minutes, to which MI-101 strain isolated in Example 1 described below was inoculated, and cultivated at 50° C. for 24 hours with shaking. After the cultivation, microbial cells were collected from the culture broth by centrifugation (3,000×g, 4° C., 20 minutes), and washed with buffer A [composition: 200 mM potassium phosphate buffer (pH 7.2), 0.5 mM dithiothreitol (threo-1,4-dimercapto-2,3-butanediol)].

The obtained microbial cells were resuspended in buffer A (about 30%, w/v) and disrupted by sonication (Branson). Next, the disrupted microbial cells were centrifuged (12,000×g, 4° C., 30 minutes), and a supernatant was recovered as a crude enzyme solution containing maleate isomerase.

The obtained crude enzyme solution was treated with streptomycin sulfate [2.2% (w/v)] to remove nucleic acids. Subsequently, a fraction of 30–70% ammonium sulfate precipitation was recovered by an ordinary method, and it was dialyzed overnight in the buffer A (4° C.). The obtained fraction of ammonium sulfate precipitation was applied to a DEAE-Sephacel (Pharmacia) column (diameter 2.6 cm×30 cm) equilibrated with the buffer A, washed sufficiently with the buffer A, and eluted with a linear density gradient (0–0.2M) of potassium chloride. The flow rate was 2 ml/minute, and each fraction was collected in an aliquot of 10 ml. The fraction of maleate isomerase was detected routinely by measuring the maleate isomerase activity. The enzyme activity was assayed at 45° C. by measuring the decrease in absorbance of meleic acid at 240 nm using a spectrophotometer (DU 7500 produced by Beckman) in the presence of fumarase (produced by Boehringer Mannheim) originating from swine heart in accordance with a method of Otsuka et al. [*Agric. Biol. Chem.*, Vol. 25, p. 726 (1961)].

The obtained active fraction containing the maleate isomerase was concentrated by using an ultrafiltration unit (UHP-43K produced by Toyo Roshi, fractionating molecular weight: 20,000), thereafter applied to a gel filtration column (Sephacryl S-200 produced by Pharmacia, φ1.6×60 cm) equilibrated with the buffer A, and eluted at a flow rate of 0.5 ml. The active fraction was detected by a similar method as that described above. Next, the obtained active fraction was applied to an anion exchange column (Mono-Q produced by Pharmacia, φ1×10 cm) equilibrated with the buffer A, and eluted with a linear density gradient (0–1M) of potassium chloride. The active fraction thus obtained was used as a purified fraction of maleate isomerase.

The purified fraction of maleate isomerase was analyzed by polyacrylamide gel electrophoresis in accordance with the method of Davis and the method of Laemmli described above, and stained with a Coomassie Blue dye solution [composition: 0.2% (v/v) Coomassie Brilliant Blue R 250, 40% (v/v) methanol, 10% (v/v) acetic acid]. As a result, a single band was detected by any of the methods.

(2) Measurement of maleate isomerase activity

A solution (50 µl) of purified maleate isomerase obtained in the item (1) described above was added to the buffer A (1850 µl), and maintained at a temperature of 50° C., solution of 200 mM disodium maleate (100 µl) was added and mixed to start the reaction. The maleate isomerase activity was determined by measuring the increase in absorbance of formed fumarate at 290 nm for 5 minutes by using a spectrophotometer (DU-7500 produced by Beckman). In the same manner, the maleate at 40° C. and 60° C. The maleate isomerase activity at each temperature was calculated as a relative activity when the activity at 50° C. was regarded as 100. A result is shown in Table 1.

TABLE 1

| Maleate isomerase activity of MI-101 strain | |
|---|---|
| Reaction temperature (°C.) | Relative activity |
| 40 | 67 |
| 50 | 100 |
| 60 | 130 |

According to the result in Table 1, it has been confirmed that the maximum activity of this maleate isomerase is provided at not less than 50° C.

Test Example 2: Purification of maleate isomerase produced by *Bacillus stearothermophilus* MI-102 strain, and measurement of activity at not less than 50° C.

(1) Purification of maleate isomerase

In the same manner as Test Example 1, MI-102 strain isolated in Example 1 described below was cultivated. A crude enzyme solution was prepared from obtained microbial cells, and then maleate isomerase was purified to obtain a purified fraction.

(2) Measurement of maleate isomerase activity

In the same manner as Test Example 1, the maleate isomerase activity was measured at 40° C., 50° C., and 60° C. for the purified maleate isomerase fraction obtained in the item (1) described above. The value of the activity at each temperature was calculated as a relative activity when an activity at 50° C. was regarded as 100. A result is shown in Table 2.

TABLE 2

| Maleate isomerase activity of MI-102 strain | |
|---|---|
| Reaction temperature (°C.) | Relative activity |
| 40 | 80 |
| 50 | 100 |
| 60 | 120 |

According to the result in Table 2, it has been confirmed that the maximum activity of this maleate isomerase is provided at not less than 50° C.

Test Example 3: Purification of maleate isomerase produced by Bacillus brevis MI-103 strain, and measurement of activity at not less than 50° C.

(1) Purification of maleate isomerase

In the same manner as Test Example 1, MI-103 strain isolated in Example 1 described below was cultivated. A crude enzyme solution was prepared from obtained microbial cells, and then maleate isomerase was purified to obtain a purified fraction.

(2) Measurement of maleate isomerase activity

In the same manner as Test Example 1, the maleate isomerase activity was measured at 40° C., 50° C., and 60° C. for the purified maleate isomerase fraction obtained in the item (1) described above. The value of the activity at each temperature was calculated as a relative activity when an activity at 50° C. was regarded as 100. A result is shown in Table 3.

TABLE 3

Maleate isomerase activity of MI-103 strain

| Reaction temperature (°C.) | Relative activity |
| --- | --- |
| 40 | 72 |
| 50 | 100 |
| 60 | 110 |

According to the result in Table 3, it has been confirmed that the maximum activity of this maleate isomerase is provided at not less than 50° C.

Test Example 4: Purification of maleate isomerase produced by Bacillus brevis MI-104 strain, and measurement of activity at not less than 50° C.

(1) Purification of maleate isomerase

In the same manner as Test Example 1, MI-104 strain isolated in Example 1 described below was cultivated. A crude enzyme solution was prepared from obtained microbial cells, and then maleate isomerase was purified to obtain a purified fraction.

(2) Measurement of maleate isomerase activity

In the same manner as Test Example 1, the maleate isomerase activity was measured at 40° C., 50° C., and 60° C. for the purified maleate isomerase fraction obtained in the item (1) described above. The value of the activity at each temperature was calculated as a relative activity when an activity at 50° C. was regarded as 100. A result is shown in Table 4.

TABLE 4

Maleate isomerase activity of MI-104 strain

| Reaction temperature (°C.) | Relative activity |
| --- | --- |
| 40 | 68 |
| 50 | 100 |
| 60 | 110 |

According to the result in Table 4, it has been confirmed that the maximum activity of this maleate isomerase is provided at not less than 50° C.

Test Example 5: Purification of maleate isomerase produced by Bacillus sp. MI-105 strain, and measurement of activity at not less than 50° C.

(1) Purification of maleate isomerase

In the same manner as Test Example 1, MI-105 strain isolated in Example 1 described below was cultivated. A crude enzyme solution was prepared from obtained microbial cells, and then maleate isomerase was purified to obtain a purified fraction.

(2) Measurement of maleate isomerase activity

In the same manner as Test Example 1, the maleate isomerase activity was measured at 40° C., 50° C., and 60° C. for the purified maleate isomerase fraction obtained in the item (1) described above. The value of the activity at each temperature was calculated as a relative activity when an activity at 50° C. was regarded as 100. A result is shown in Table 5.

TABLE 5

Maleate isomerase activity of MI-105 strain

| Reaction temperature (°C.) | Relative activity |
| --- | --- |
| 40 | 65 |
| 50 | 100 |
| 60 | 113 |

According to the result in Table 5, it has been confirmed that the maximum activity of this maleate isomerase is provided at not less than 50° C.

2. Method of producing L-aspartic acid

The method of producing L-aspartic acid according to the present invention comprises the steps of reacting a culture of a microorganism which produces maleate isomerase or a treated product thereof, a culture of a microorganism which produces aspartase or a treated product thereof, maleic acid, and ammonia in an aqueous solution, producing L-aspartic acid from maleic acid and ammonia by enzyme reactions in the reaction mixture, and collecting L-aspartic acid from the reaction mixture.

All of the microorganisms which produce maleate isomerase can be used in the present invention. For example, microorganisms which produce maleate isomerase belonging to the genera Alcaligenes, Pseudomonas, and Xanthomonas are used. Preferably, there are exemplified *Alcaligenes faecalis, Alcaligenes eutrophus, Pseudomonas fluolescens*, and *Xanthomonas maltophilia*. More preferably, there are exemplified microbial strains such as *Alcaligenes faecalis* IFO 12669, *Alcaligenes faecalis* IFO 13111, *Alcaligenes faecalis* IAM 1473, *Pseudomonas fluolescens* ATCC 23728, and *Xanthomonas maltophilia* ATCC 13270.

Especially, it is preferable to use microorganisms belonging to the genus Bacillus capable of growing at a temperature above 40° C. as the microorganism which produces maleate isomerase, because L-aspartic acid can be produced under a high temperature condition. Such microorganisms belonging to the genus Bacillus are exemplified by *Bacillus stearothermophilus*, and *Bacillus brevis*. More preferably, there are exemplified microbial strains such as *Bacillus stearothermophilus* MI-101, *Bacillus stearothermophilus* MI-102, *Bacillus brevis* MI-103, *Bacillus brevis* MI-104, and *Bacillus* sp. MI-105 described above.

All of the microorganism which produces aspartase can be also used in the present invention. For example, microorganisms which produce aspartase belonging to the genera Brevibacterium, Escherichia, Pseudomonas, and Bacillus are used. Preferably, there are exemplified *Brevibacterium flavum* MJ-233 (FERM BP-1497), *Brevibacterium flavum* MJ-233-AB-41 (FERM BP-1498), *Brevibacterium ammoniagenes* ATCC 6872, *Escherichia coli* ATCC 11303, *Escherichia coli* ATCC 27325, etc.

The microorganism which produces maleate isomerase can be cultivated in a per se known manner and usually used medium added with natural nutrients such as meat extract, yeast extract, and peptone. To the medium, if necessary, it is possible to add ammonium salt such as ammonium chloride, ammonium sulfate, and ammonium phosphate; nitrate salt such as sodium nitrate, potassium nitrate, and ammonium nitrate; and ammonia as a nitrogen source; and potassium phosphate, magnesium sulfate, iron, manganese, zinc, copper, etc. as an inorganic substance.

In order to enhance the maleate isomerase activity, it is desirable to add maleic acid or malonic acid to the medium. It is suitable that maleic acid or malonic acid is added at a concentration in a range of 10–200 mM, preferably 50–100 mM.

The microorganism which produces aspartase can be also cultivated in a per se known manner and usually used medium added with natural nutrients such as meat extract, yeast extract, and peptone. Glucose and ethanol can be added as a carbon source. To the medium, if necessary, it is possible to add ammonium salt such as ammonium chloride, ammonium sulfate, and ammonium phosphate; nitrate salt such as sodium nitrate, potassium nitrate, and ammonium nitrate; and ammonia as a nitrogen source; and potassium phosphate, magnesium sulfate, iron, manganese, zinc, copper, etc. as an inorganic substance.

The microorganism which produces maleate isomerase and the microorganism which produces aspartase described above are cultivated under an aerobic condition with aeration, agitation, shaking, etc. It is suitable that the cultivation temperature is 25°–40° C., preferably 28°–35° C. pH during the cultivation can be maintain at a range of 6–9. pH can be adjusted during the cultivation by adding acid or alkali.

The method of the present invention comprises the steps of reacting both of a culture of a microorganism which produces maleate isomerase or a treated product thereof and a culture of a microorganism which produces aspartase or a treated product thereof with maleic acid and ammonia in an aqueous solution, producing L-aspartic acid from maleic acid and ammonia by enzyme reactions in the aqueous solution, and collecting L-aspartic acid from the reaction mixture.

The "culture" herein refers to microbial cells obtained from the medium after cultivating the microorganism. The "treated product" means an immobilized product obtained by immobilizing the culture from the medium, ruptured product obtained by sonicating the microbial cells by means of sonication, crush and so on, an extracted material obtained by extracting the ruptured material with water or the like, crude enzyme or purified enzyme of maleate isomerase or aspartase obtained by subjecting the extracted material to treatments of ammonium sulfate salting out, column chromatography and so on, and an immobilized material obtained by immobilizing the ruptured material, the extracted material, the enzyme component and so on.

The concept of "reacting both of a culture of a microorganism which produces maleate isomerase or a treated preparation thereof, a culture of a microorganism which produces aspartase or a treated product thereof, maleic acid, and ammonia in an aqueous solution" includes addition of a culture of each microorganism or a treated product thereof to an aqueous solution containing maleic acid and ammonia, addition of maleic acid and ammonia to an aqueous solution containing a culture of each microorganism or a treated preparation thereof, and passage through of an aqueous solution containing maleic acid and ammonia to a column charged with each immobilized microorganism or a treated product thereof.

Microbial cells may be used as they are after recovering the culture, or as washed cells washed with an appropriate buffer, for example, about 0.05–0.2M of a phosphate buffer (pH 6–9). The enzyme reactions can be conducted concurrently with the cultivation of the aforementioned microorganisms.

The "treated product" described above means an immobilized material obtained by immobilizing the culture or microbial cells recovered therefrom, a ruptured material obtained by sonicating the microbial cells by means of sonication, crush and so on, an extracted material obtained by extracting the ruptured material with water or the like, enzyme components obtained by subjecting the extracted material to treatments of ammonium sulfate salting out, column chromatography and so on, and an immobilized material obtained by immobilizing the ruptured material, the extracted material, the enzyme components and so on. Microbial cells, etc. can be immobilized by a method of immobilization to an appropriate material such as acrylamide monomer, alginic acid, or carageenan in accordance with a per se known and usually used method, for example, the method described in the aforementioned item 1. (3) or the like.

The method of allowing the microorganism which produces maleate isomerase or a treated product thereof and the microorganism which produces aspartase or a treated product thereof to act in an aqueous solution containing maleic acid and ammonia includes, for example, a fermentative method and an enzymatic method. The "fermentative method" herein refers to a method in which an objective substance is produced while accompanying growth of microorganisms under a condition (temperature, pH) capable of growing of the microorganisms in an aqueous medium containing components which enable the microorganisms used to proliferate. The "enzymatic method" refers to a method in which an objective substance is produced in an aqueous reaction mixture which does not contain all of components required for the growth by using obtained microbial cells or a treated product thereof after cultivating microorganisms used by means of an appropriate cultivative method.

In the case of the fermentative method, the culture or microbial cells are used as the microorganism which produces maleate isomerase and the microorganism which produces aspartase. A medium obtained by adding maleic acid and ammonia to the medium as described above is used as the aqueous solution.

The concentrations of maleic acid and ammonia in the medium are not specifically limited provided that the aforementioned two types of microorganisms can produce L-aspartic acid. However, it is suitable that the concentration of maleic acid is usually in a range of 1–40% (wt/vol), preferably 5–20% (wt/vol), and that the concentration of ammonia is usually in a range of 0.2–8M, preferably 1–4M. Maleic acid and ammonia can be added to the medium collectively or successively. In a continuous reaction, the reaction can be conducted while maintaining the concentration of maleic acid to be about 0.01–1%.

The cultivation temperature is appropriately 10°–60° C., preferably 30°–50° C. pH of the medium during cultivation can be about 6–9. pH can be adjusted by adding acid or alkali. The cultivation can be performed usually for about 10–72 hours under an aerobic condition with aeration, agitation, shaking, etc.

L-aspartic acid can be produced and accumulated in a considerable amount in the medium by performing the cultivation as described above.

In the case of the enzymatic method, microbial cells or a treated product thereof as described above is used as the microorganism which produces maleate isomerase or the treated product thereof and the microorganism which produces aspartase or the treated product thereof. An aqueous solution or an appropriate buffer, for example, a phosphate buffer of about 0.05–0.2M containing at least maleic acid and ammonia is used as the aqueous solution.

The amount of use of the microbial cells or the treated product thereof prepared as described above is not specifically limited. However, it is suitably 0.5–30% (wt/vol) for each on the basis of the volume of the aqueous solution.

The concentrations of maleic acid and ammonia in the aqueous solution are not specifically limited provided that maleic acid and ammonia are converted by the enzymatic method to enable production of L-aspartic acid. However, it is suitable that the concentration of maleic acid is usually in a range of 1–40% (wt/vol), preferably 5–20% (wt/vol), and that the concentration of ammonia is usually in a range of 0.2–8M, preferably 1–4M. Maleic acid and ammonia can be added to the aqueous solution collectively or successively.

Divalent metal salts such as calcium salt, magnesium salt, and manganese salt can be added to the aqueous solution, if necessary.

It is suitable that the enzyme reaction temperature in the aforementioned aqueous solution is usually in a range of 20°–60° C., preferably 25°–50° C. pH of the aqueous solution during the reaction can be 6–10, preferably about 7–9. pH can be adjusted by adding acid or alkali to the aqueous solution. The enzyme reactions can be usually performed for 10–72 hours with agitation or shaking.

L-aspartic acid can be produced and accumulated in a considerable amount in the aqueous solution by performing the enzyme reactions as described above.

In the present invention, the isomerization reaction from maleic acid to fumaric acid proceeds concurrently with the reaction to produce L-aspartic acid from fumaric acid and ammonia. Accordingly, the concentration of fumaric acid in the reaction solution can be suppressed within a certain range, and L-aspartic acid is produced efficiently. Especially, it is preferable that the concentration of fumaric acid in the reaction solution is maintained at not more than 0.5% (wt/vol). It is sufficient that the concentration of fumaric acid is maintained at not more than 0.5% (wt/vol) for almost all period of time during the reaction. No special problem occurs even if this concentration is instantly exceeded. In order to maintain the concentration of fumaric acid to be not more than 0.5% (wt/vol), the aspartase activity may be allowed not to become too small relatively as compared with the maleate isomerase activity, for which, for example, there may be used methods of maintaining pH at an alkaline side, raising the concentration of ammonia, adding an excessive amount of the microorganism which produces aspartase as compared with the microorganism which produces maleate isomerase and so on.

After producing and accumulating L-aspartic acid in the aqueous solution as described above, L-aspartate can be recovered from the aqueous solution in accordance with per se known and usually used separation and purification methods. For example, L-aspartic acid can be recovered as crystals by precipitation and separation by sulfate isoelectric precipitation or the like, followed by washing with water and drying.

According to the method of the present invention, L-aspartic acid can be produced from maleic acid and ammonia efficiently at a high yield.

DESCRIPTION OF PREFERRED EMBODIMENTS

Next, the present invention will be more specifically explained with reference to Examples. However, Examples described below are referred to only in aid of obtaining concrete recognition of the present invention, and the scope of the present invention is not limited thereby at all.

EXAMPLE 1

Isolation of microorganisms which produce maleate isomerase exhibiting maximum activities at not less than 50° C.

(1) Isolation of maleate-assimilating microorganisms

Soil samples collected from nature were put into 10 ml of medium A [composition: disodium maleate 5 g, $KH_2PO_4$ 0.7 g, $K_2HPO_4$ 1.4 g, $NH_4NO_3$ 1 g, $MgSO_4.7H_2O$ 0.2 g, biotin 0.2 mg, thiamin hydrochloride 0.2 mg, $FeSO_4.7H_2O$ 20 mg, $MnSO_4$ 20 mg, distilled water 1 L (pH 7.2)], and cultivated aerobically with shaking at 50° C. for 3 days. The culture (1 ml) was successively inoculated to 10 ml of the medium A, and cultivated with shaking in the same manner for further 3 days. The culture after cultivation was spread on a plate medium containing 2% agar having the composition of the medium A described above, and cultivated at 50° C. for 2 days. Colonies grown on the plate medium were isolated.

(2) Selection of maleate isomerase-producing microorganisms

The microorganisms isolated in the item (1) described above were cultivated with shaking at 50° C. for 1 day by using 100 ml of the medium A described above, and microbial cells were harvested by centrifugation (3,000×g, 4° C., 20 minutes), followed by washing with 0.9% (w/v) NaCl. Subsequently washed bacterial cells were suspended in 1 ml of the aforementioned NaCl solution, added with 1 ml of reaction solution A [composition: sodium maleate 84 g/l, Triton X-100 1 g/l], and then shaken at 50° C. overnight. A supernatant was recovered by centrifugation. The obtained supernatant of the reaction solution was analyzed by high-performance liquid chromatography analysis (LC-5A produced by Shimadzu) equipped with an organic acid analysis column (SCR-101H column produced by Shimadzu) and a UV detector (210 nm). Among the microorganisms isolated in the item (1) described above, maleate isomerase-producing microorganisms were selected as microorganisms which presented a peak of fumaric acid in addition to a peak of maleic acid as a substrate.

Five strains among the maleate isomerase-producing microorganisms obtained by the aforementioned separation operation were further investigated for their bacteriological properties as described above. As a result, it was revealed that each of them was a novel strain. They were designated as *Bacillus stearothermophilus* MI-101, *Bacillus stearothermophilus* MI-102, *Bacillus brevis* MI-103, *Bacillus brevis* MI-104, and *Bacillus sp.* MI-105, respectively.

EXAMPLE 2

Production of fumaric acid by *Bacillus stearothermophilus* MI-101

The medium A described above (3 L) was introduced into a jar fermenter having a volume of 5 L, and sterilized at 121° C. for 20 minutes, to which MI-101 strain isolated in Example 1 described above was inoculated, and cultivated with shaking at 50° C. for 1 day. After the cultivation, microbial cells were recovered from a culture liquid by centrifugation (3,000××g, 4° C., 20 minutes), and washed with 0.9% (w/v) NaCl. Subsequently 5 g (wet weight) of the washed microbial cells were suspended in 50 ml of 0.9% (w/v) NaCl solution, added with 50 ml of reaction solution A [composition: sodium maleate 84 g/l, Triton X-100 1 g/l], and then shaken at 45° C. for 24 hours. After the reaction, a supernatant was recovered by centrifugation. The obtained supernatant of the reaction solution was analysed by high-performance liquid chromatography analysis (LC-5A produced by Shimadzu) equipped an organic acid analysis column (SCR-101H column produced by Shimadzu) and a UV detector (210 nm). As a result, it was confirmed that 23 g/L of fumaric acid was formed. Fumaric acid was quantitatively determined by using pimelic acid as an internal standard substance.

Crystals of fumaric acid (about 2.2 g) were obtained by adding conc. sulfuric acid to the aforementioned reaction solution to make it acidic.

EXAMPLE 3

Production of fumaric acid by *Bacillus stearothermophilus* MI-102

MI-102 strain isolated in Example 1 described above was inoculated, and cultivated with shaking at 50° C. for 1 day in the same manner as Example 2 described above. Microbial cells were recovered by centrifugation, and then washed with 0.9% (w/v) NaCl. Subsequently 5 g (wet weight) of the washed microbial cells were suspended in 50 ml of 0.9% (w/v) NaCl solution, added with 50 ml of the aforementioned reaction solution A, and then shaken at 45° C. for 24 hours. After the reaction, an obtained supernatant of the reaction solution was subjected to high-performance liquid chromatography analysis (LC-5A produced by Shimadzu) in the same manner as Example 2 described above. As a result, it was confirmed that 25 g/L of fumaric acid was produced.

Crystals of fumaric acid (about 2.3 g) were obtained by adding conc. sulfuric acid to the aforementioned reaction solution to make it acidic.

EXAMPLE 4
Production of fumaric acid by *Bacillus brevis* MI-103

MI-103 strain isolated in Example 1 described above was inoculated, and cultivated with shaking at 50° C. for 1 day in the same manner as Example 2 described above. Microbial cells were recovered by centrifugation, and then washed with 0.9% (w/v) NaCl. Subsequently 5 g (wet weight) of the washed microbial cells were suspended in 50 ml of 0.9% (w/v) NaCl solution, added with 50 ml of the aforementioned reaction solution A, and then shaken at 45° C. for 24 hours. After completion of the reaction, an obtained supernatant of the reaction solution was analyzed by high-performance liquid chromatography analysis (LC-5A produced by Shimadzu) in the same manner as Example 2 described above. As a result, it was confirmed that 20 g/L of fumaric acid was produced.

Crystals of fumaric acid (about 1.9 g) were obtained by adding conc. sulfuric acid to the aforementioned reaction solution to make it acidic.

EXAMPLE 5
Production of fumaric acid by *Bacillus brevis* MI-104

MI-104 strain isolated in Example 1 described above was inoculated, and cultivated with shaking at 50° C. for 1 day in the same manner as Example 2 described above. Microbial cells were recovered by centrifugation, and then washed with 0.9% (w/v) NaCl. Subsequently 5 g (wet weight) of the washed microbial cells were suspended in 50 ml of 0.9% (w/v) NaCl solution, added with 50 ml of the aforementioned reaction solution A, and then shaken at 45° C. for 24 hours. After the reaction, an obtained supernatant of the reaction solution was analyzed by high-performance liquid chromatography analysis (LC-5A produced by Shimadzu) in the same manner as Example 2 described above. As a result, it was confirmed that 19 g/L of fumaric acid was produced.

Crystals of fumaric acid (about 2.1 g) were obtained by adding conc. sulfuric acid to the aforementioned reaction solution to make it acidic.

EXAMPLE 6
Production of fumaric acid by Bacillus sp. MI-105

MI-105 strain isolated in Example 1 described above was inoculated, and cultivated with shaking at 50° C. for 1 day in the same manner as Example 2 described above. Microbial cells were recovered by centrifugation, and then washed with 0.9% (w/v) NaCl. Subsequently 5 g (wet weight) of the washed microbial cells were suspended in 50 ml of 0.9% (w/v) NaCl solution, added with 50 ml of the aforementioned reaction solution A, and then shaken at 45° C. for 24 hours. After the reaction, an obtained supernatant of the reaction solution was analyzed by high-performance liquid chromatography analysis (LC-5A produced by Shimadzu) in the same manner as Example 2 described above. As a result, it was confirmed that 23 g/L of fumaric acid was produced.

Crystals of fumaric acid (about 2.3 g) were obtained by adding conc. sulfuric acid to the aforementioned reaction solution to make it acidic.

EXAMPLE 7
Production of L-aspartic acid (1) Cultivation of malate isomerase-producing microorganism An aliquot (100 ml) of a medium containing 10 g of meat extract, 10 g of peptone, 5 g of NaCl, 10 g of maleic acid, and 1000 ml of distilled water (with pH adjusted to 7.0 with sodium hydroxide) in an Erlenmeyer flask having a volume of 500 ml, and sterilized at 120° C. for 20 minutes. A microbial strain of *Alcaligenes faecalis* IFO 12669 was inoculated to the medium, and cultivated with shaking at 30° C. for 24 hours.

The same medium as that described above (1,500 ml) was put into a jar fermenter having a volume of 3 L, and sterilized at 120° C. for 20 minutes, to which 30 ml of a culture medium obtained by cultivation with shaking as described above was inoculated, and cultivated at 30° C. for 24 hours. An obtained culture liquid was centrifuged (8,000 rpm, 15 minutes, 4° C.) to collect microbial cells which were washed once with 0.1M phosphate buffer (pH 7.0), and subjected to the following reaction.

(2) Cultivation of aspartase-producing microorganism

An aliquot (100 ml) of a medium containing 4 g of urea, 14 g of $(NH_4)_2SO_4$, 0.5 g of $KH_2PO_4$, 0.5 g of $K_2HPO_4$, 0.5 g of $MgSO_4 \cdot 7H_2O$, 20 mg of $FeSO_4 \cdot 7H_2O$, 20 mg of $MnSO_4 \cdot nH_2O$, 200 µg of D-biotin, 100 µg of thiamin hydrochloride, 1 g of yeast extract, and 1 g of casamino acid to give a total volume of 1,000 ml by adding distilled water (pH 6.6) was poured into an Erlenmeyer flask having a volume of 500 ml, and sterilized at 120° C. for 15 minutes. A sterilized 50% aqueous glucose solution (4 ml) was added to the medium. A microbial strain of *Brevibacterium flavum* MJ-233-AB-41 (FERM BP-1498) was inoculated thereto, and cultivated with shaking at 33° C. for 24 hours.

The same medium as that described above (1,000 ml) was put into a jar fermenter having a volume of 2 L, and sterilized at 120° C. for 20 minutes. A culture liquid (20 ml) obtained by cultivation with shaking as described above, and a sterilized 50% aqueous glucose solution (200 ml) were added thereto, and cultivated at 33° C. for 24 hours. An obtained culture liquid was centrifuged (8,000 rpm, 15 minutes, 4° C.) to collect microbial cells. Next, the collected microbial cells were suspended in an aqueous solution containing 100 g of aspartic acid, 180 ml of ammonia, 2.2 g of calcium chloride, and 0.8 g of polyoxyethylenesorbitan monolaurate (trade name: Tween 20) to give a total volume of 1,000 ml by adding water, and shaken at 45° C. for 3 hours. Subsequently the microbial cells were recovered by centrifugation (8,000 rpm, 15 minutes, 4° C.), and thus the malate-by-producing activity contaminating the microbial cells was removed.

(3) Production of L-aspartic acid from maleic acid and ammonia

The both microbial cells recovered in the items (1) and (2) described above (40 g of IFO 12669 strain, and 120 g of MJ-233-AB-41 strain) were added to a reaction solution [aqueous solution containing 100 g of maleic acid and 132 ml of 25% aqueous ammonia to give a total volume of 500 ml by adding water (pH 8)], and reacted at 30° C. for 24 hours. During this reaction, the concentration of fumaric acid in the reaction solution was generally maintained at 0.2% (wt/vol).

As a result of quantitative determination of the amount of L-aspartic acid in the reaction solution by using high-performance liquid chromatography, L-aspartic acid was obtained from 100 g of maleic acid at a molar yield of not less than 99% of a theoretical yield. After the reaction, aspartic acid was precipitated by adding sulfuric acid to ammonium L-aspartate, and washed with water followed by drying to obtain crystals of L-aspartic acid. The amount of the obtained crystals was 112 g.

Reference Example (1) Cultivation of microorganism having ability to isomerize maleic acid A microbial strain of *Alcaligenes faecalis* IFO 12669 was cultivated in the same manner as Example 7, and microbial cells were obtained.

(2) Cultivation of aspartase-producing microorganism

An aliquot (100 ml) of a medium containing 4 g of urea, 14 g of $(NH_4)_2SO_4$, 0.5 g of $KH_2PO_4$, 0.5 g of $K_2HPO_4$, 0.5 g of $MgSO_4.7H_2O$, 20 mg of $FeSO_4.7H_2O$, 20 mg of $MnSO_4.nH_2O$, 200 µg of D-biotin, 100 µg of thiamin hydrochloride, 1 g of yeast extract, and 1 g of casamino acid to give a total volume of 1,000 ml by adding distilled water (pH 6.6) was poured into an Erlenmeyer flask having a volume of 500 ml, and sterilized at 120° C. for 15 minutes. A sterilized 50% aqueous glucose solution (4 ml) was added to the medium. A microbial strain of *Brevibacterium flavum* MJ-233-AB-41 (FERM BP-1498) was inoculated thereto, and cultivated with shaking at 33° C. for 24 hours.

The same medium as that described above (1,000 ml) was introduced into a jar fermenter having a volume of 2 L, and sterilized at 120° C. for 20 minutes. A culture liquid (20 ml) obtained by cultivation with shaking as described above, and a sterilized 50% aqueous glucose solution (100 ml) were added thereto, and cultivated at 33° C. for 24 hours. An obtained culture liquid was centrifuged (8,000 rpm, 15 minutes, 4° C.) to collect microbial cells. Next, the collected microbial cells were suspended in an aqueous solution containing 100 g of aspartic acid, 180 ml of ammonia, 2.2 g of calcium chloride, and 0.8 g of polyoxyethylenesorbitan monolaurate (trade name: Tween 20) to give a total volume of 1,000 ml by adding water, and shaken at 45° C. for 3 hours. Subsequently the microbial cells were recovered by centrifugation (8,000 rpm, 15 minutes, 4° C.), and thus the malate-by-producing activity contaminating the microbial cells was removed.

(3) Production of L-aspartic acid from maleic acid and ammonia

The both microbial cells recovered in the items (1) and (2) described above (40 g of IFO 12669 strain, and 60 g of MJ-233-AB-41 strain) were added to a reaction solution [aqueous solution containing 100 g of maleic acid and 132 ml of 25% aqueous ammonia to give a total volume of 500 ml by adding water (pH 8)], and reacted at 30° C for 24 hours. During this reaction, the concentration of fumaric acid in the reaction solution was generally maintained at 0.6% (wt/vol).

As a result of quantitative determination of the amount of L-aspartic acid in the reaction solution by using high-performance liquid chromatography, L-aspartic acid was obtained from 100 g of maleic acid at a molar yield of 95% of a theoretical yield. After the reaction, aspartic acid was precipitated by adding sulfuric acid to ammonium L-aspartate, and washed with water followed by drying to obtain crystals of L-aspartic acid. The amount of the obtained crystals was 105 g.

EXAMPLE 8

Production of aspartic acid from maleic acid using Bacillus stearothermophilus MI-101

The medium A described above (3 L) was put into a jar fermenter having a volume of 5 L, and sterilized at 121° C. for 20 minutes. MI-101 strain isolated in Example 1 described above was inoculated thereto, and cultivated with shaking at 50° C. for 1 day. After the cultivation, microbial cells were recovered from a culture bloth by centrifugation (3,000×g, 4° C., 20 minutes), and washed with 0.9% (w/v) NaCl.

On the other hand, *Brevibacterium flavum* MJ-233 (FERM BP-1497) as an aspartase-producing microorganism was cultivated in the same manner at 30° C. until its late logarithmic growth phase by using 3 L of medium B [composition: 2 g of urea, 7 g of $(NH_4)_2SO_4$, 0.5 g of $K_2HPO_4$, 0.5 g of $KH_2PO_4$, 0.5 g of $MgSO_4$, 6 mg of $FeSO_4.7H_2O$, 6 mg of $MnSO_4.4–6H_2O$, 2.5 g of yeast extract, 5 g of casamino acid, 200 µg of biotin, 200 µg of thiamin hydrochloride, 20 g of glucose, and 1 L of distilled water]. Microbial cells were collected by centrifugation, and washed with 0.9% (w/v) NaCl.

Next, the both washed bacterial cells (each 5 g, wet weight) of the MI-101 and MJ-233 strains obtained as described above were respectively suspended in 50 ml of a 0.9% (w/v) NaCl solution. A reaction solution (50 ml) [composition: 30 g of maleic acid, 40 ml of 25% aqueous ammonia, 0.5 g of Triton X-100, and 1 L of distilled water] was added thereto, and shaken at 45° C. for 24 hours. After completion of the reaction, a supernatant solution was recovered by centrifugation. The obtained supernatant of the reaction solution was subjected to thin-layer chromatography [developing solvent: n-butanol-acetic acid-water=4:1:1 (volume ratio), coloring agent: ninhydrin agent]. As a result, it was confirmed that about 25 g/L of aspartic acid was produced.

EXAMPLE 9

Production of aspartic acid from maleic acid using *Bacillus stearothermophilus* MI-102

L-aspartic acid was produced in the same manner as Example 8 except that *Bacillus stearothermophilus* MI-102 was used as a maleate isomerase-producing microorganism. As a result, it was confirmed that about 25 g/L of aspartic acid was produced.

EXAMPLE 10

Production of aspartic acid from maleic acid using *Bacillus brevis* MI-103

L-aspartic acid was produced in the same manner as Example 8 except that *Bacillus brevis* MI-103 was used as a maleate isomerase-producing microorganism. As a result, it was confirmed that about 20 g/L of aspartic acid was produced.

EXAMPLE 11

Production of aspartic acid from maleic acid using *Bacillus brevis* MI-104

L-aspartic acid was produced in the same manner as Example 8 except that *Bacillus brevis* MI-104 was used as a maleate isomerase-producing microorganism. As a result, it was confirmed that about 19 g/L of aspartic acid was produced.

EXAMPLE 12

Production of aspartic acid from maleic acid using Bacillus sp. MI-105

L-aspartic acid was produced in the same manner as Example 8 except that Bacillus sp. MI-105 was used as a maleate isomerase-producing microorganism. As a result, it was confirmed that about 23 g/L of aspartic acid was produced.

What is claimed is:

1. A method of producing fumaric acid comprising the steps of:

reacting a culture of a microorganism capable of growing at a temperature above 40° C., and which produces maleate isomerase that exhibits a maximum activity at not less than 50° C. or a treated product of said culture having maleate isomerase activity and obtained by subjecting the culture to at least one treatment selected from the group consisting of immobilization, rupture, extraction and purification with maleic acid in an aqueous solution; and isomerizing maleic acid by an enzyme reaction in said reaction mixture to produce fumaric acid, said microorganism being selected form the group consisting of *Bacillus stearothermophilus, Bacillus brevis* and Bacillus sp. MI-105.

2. The method of producing fumaric acid according to claim 1, wherein the step of reacting is carried out by reacting the culture of the microorganism with maleic acid in the aqueous solution.

3. The method of producing fumaric acid according to claim 1, wherein said microorganism is *Bacillus stearothermophilus*.

4. The method of producing fumaric acid according to claim 1, wherein said microorganism is *Bacillus brevis*.

5. The method of producing fumaric acid according to claim 3, wherein said microorganism is *Bacillus stearothermophilus* MI-101.

6. The method of producing fumaric acid according to claim 3, wherein said microorganism is *Bacillus stearothermophilus* MI-102.

7. The method of producing fumaric acid according to claim 4, wherein said microorganism is *Bacillus brevis* MI-103.

8. The method of producing fumaric acid according to claim 4, wherein said microorganism is *Bacillus brevis* MI-104.

9. The method of producing fumaric acid according to claim 1, wherein said microorganism is Bacillus sp. MI-105.

10. A method of producing fumaric acid comprising the step of:

isomerizing maleic acid with maleate isomerase that exhibits a maximum activity at not less than 50° C. in an aqueous solution to produce fumaric acid, said maleate isomerase being produced by a microorganism capable of growing at a temperature above 40° C., said microorganism being selected from the group consisting of *Bacillus stearothermoohilus, Bacillus brevis* and Bacillus sp. MI-105.

11. The method of producing fumaric acid according to claim 10, wherein the step of isomerizing is carried out by reacting a culture of said microorganism with maleic acid in the aqueous solution.

* * * * *